United States Patent [19]
Mack

[11] Patent Number: 5,724,746
[45] Date of Patent: Mar. 10, 1998

[54] DENTAL RECORDING APPARATUS

[76] Inventor: Heinz Mack, Taxisstr. 41, D-80637 München, Germany

[21] Appl. No.: 558,655

[22] Filed: Nov. 16, 1995

[30] Foreign Application Priority Data

Nov. 25, 1994 [DE] Germany .......................... 44 41 991.0

[51] Int. Cl.⁶ ............................................. A61C 19/045
[52] U.S. Cl. ........................... 033/514; 433/69; 433/73
[58] Field of Search .............................. 33/23.09, 511, 33/512, 513, 514; 433/68, 69, 73, 55, 56

[56] References Cited

U.S. PATENT DOCUMENTS

| | | | |
|---|---|---|---|
| 1,052,806 | 2/1913 | Evans | 433/73 |
| 2,455,451 | 12/1948 | Tully | 33/513 |
| 2,829,435 | 4/1958 | Kazis et al. | 433/69 |
| 3,056,210 | 10/1962 | De Pietro | 33/514 |
| 3,256,523 | 6/1966 | De Pietro | 33/513 |
| 4,126,938 | 11/1978 | Lee | 433/69 |
| 4,328,620 | 5/1982 | Mack et al. | 33/514 |
| 4,354,836 | 10/1982 | Santoni | 433/73 |
| 4,537,574 | 8/1985 | Clark | 433/69 |
| 4,561,846 | 12/1985 | Polizzotto | 433/69 |
| 5,078,600 | 1/1992 | Austin | 433/73 |

*Primary Examiner*—Thomas B. Will
*Attorney, Agent, or Firm*—Larson & Taylor

[57] ABSTRACT

A dental recording apparatus for recording the movements of the jaw joints in relation to the skull includes (A) an adjustable upper recording bow which is secured on the bridge of the nose, the top of the skull and the sides of the head and which has a nose bridge support, vertical frame, rubber strap and positioning units or measuring/recording plates, and (B) a lower recording bow. The apparatus permits an exact positioning of the apparatus on the head of the patient, both in terms of an exact positioning of the upper recording bow and also of the lower recording bow. The positioning devices located on the upper recording bow has inwardly arranged earplugs, and outwardly arranged pins which are used for the coupling of the side arms of the lower recording bow, in order to be able to couple the side arms of the lower recording bow exactly at right angles, as a result of which parallelization of the lower recording bow to the upper recording bow and to the pivot axis of the jaw joints is necessarily achieved.

3 Claims, 2 Drawing Sheets

DENTAL RECORDING APPARATUS

FIELD OF THE INVENTION

The present invention relates to a dental apparatus for recording the movements of the jaw joints in relation to the skull for diagnosis of the functioning of the jaw joint system before, during and after therapeutic measures, by direct measurement and recording of the horizontal condyle path inclinations and of the Bennett values. All cephalic articulators with a defined reference plane can be adjusted exactly thereto. The recordings of the condyle path inclinations and the measurements of the lateral displacement of the lower jaw are based on the same measurement points (the hinge axis points). Axial recordings and recordings proximal to the joint do not cause any substantial distortions. The recordings from an apparatus of this type can therefore be interpreted and utilized directly, in contrast to non-axial pantography.

BACKGROUND OF THE INVENTION

Such a dental recording apparatus, which is described in U.S. Pat. No. 4,328,620, issued to Heinz Mack, the same inventor of the present invention, and to which reference is made here in full, essentially comprises (A) an adjustable upper recording bow which is secured on the bridge of the nose and on the area of the temples and which has a nose bridge support, measuring/recording plates, upper reference indicator and rubber strap, and (B) a lower recording bow which is connected to the movable lower jaw by means of a tray or a clamping arrangement, the lower recording bow having, on both side arms which are secured on the cross bar, arrangements into which a recording and measuring arrangement is introduced which permits the continuous recording of the movements in all 3 planes, i.e. which makes it possible to plot the vertical and horizontal movements and at the same time to measure the axial displacement of the horizontal movement mechanically, electronically, acoustically or optically and/or to record these via an auxiliary device.

However, in the case of this known recording apparatus, which in principle has proven to be effective in practice, it has been observed over time that the users often do not position the tracer apparatus correctly on the head of the patient, as a result of which substantial distortions can occur.

Incorrect positioning arises if:

1. the recording apparatus (fastened on the skull) is disposed to be geometrically offset with respect to the transverse pivot axis of the lower jar (hinge axis), and/or 2. the lower recording bow (fastened on the lower jaw) is not aligned exactly parallel to the upper recording frame.

SUMMARY OF THE INVENTION

The object of the present invention was therefore to improve this known dental recording apparatus in such a way that it is possible for each and every user, i.e. even the unpracticed user, to achieve an exact positioning of the dental recording apparatus on the head of the patient, both in terms of exact positioning of the upper recording bow and also of the lower recording bow.

This object was achieved by virtue of the fact that (1) the upper recording bow additionally has the following parts:

(a) positioning means with earplug located thereon for the outer ear, and pins for the positioning of the lower recording bow, the positioning arrangements being replaced later by the measuring/recording plates, (b) a perpendicularly arranged vertical frame with support bars which are connected in the upper area to an adjustable cross bar on which the head cushion is secured, and which are provided in the lower area with laterally adjustable and lockable side spacers, (c) a rear U-shaped auxiliary frame which, for the purpose of parallelization of the side arms, is adjustable to the front spacing between the side arms and is attachable on the side arms, and which consists of a cross bar and lockable longitudinal bar, and (d) a nose bridge, or nasion support which is adjustable in the longitudinal direction and which is laterally displacable on the front cross bar, and that (2) the lower recording bow for positioning on the pins of the positioning means of the upper recording bow has sleeves which are guided through the attachment at the rear end of the side arms, are fitted on the pins and are locked by means of the locking screws, and, after casting-on of the tray on the lower jaw or securing of the clamping arrangement on the lower jaw, and after positioning of the upper recording bow and of the lower recording bow, the positioning means are replaced by the measuring/recording plates and, on the lower recording bow, the sleeves are replaced by the recording and measuring arrangements.

The side arms of the upper recording bow can be displaced preferably only in the transverse direction and support the positioning means with the earplugs for the outer ear, which earplugs point inwards, in other words to the skull center, and which position and collinearize the recording apparatus with respect to the anatomy of the ear and thus to the pivot axis of the jaw points, and which thus necessarily ensure the correct arrangement of the recording apparatus in relation to the asymmetric conditions of the skull.

In addition, the positioning means also have receiving devices arranged outwardly, for example pins, which are used for the coupling of the side arms of the lower recording bow, in order to be able to couple the side arms of the lower recording bow exactly at right angles, as a result of which parallelization of the lower recording bow to the upper recording bow and to the pivot axis of the jaw joints is necessarily achieved.

Additional markings and sequential threaded holes on the side arms of the upper recording bow permit a parallel and symmetrical shifting of the disposed positioning arrangements or of the measuring/recording plates of the recording apparatus and also of the vertical frame.

In addition, the upper recording bow can be adjusted in the longitudinal direction by means of a spindle on the nose bridge support.

In addition, the upper recording bow can be used as a transfer bow, use being made of the vertical rod which can be coupled on the upper recording bow and is intended for the model support (bite fork support), and of the adjustable and telescopic reference indicator.

The upper recording bow is secured on the bridge of the nose, the temples, the upper surfaces of the head, and the back of the neck by means of a rubber strap.

The lower recording bow has adjustable side arms for the axis pins and the recording and measuring arrangements. It is anchored on the lower jaw by a stemmed tray, for example, by plaster casting. In the case of a jaw without teeth, the securing is effected using a lower jaw clamp.

After individual localization of the hinge axis points with the lower recording bow, the axis pins, for example, are replaced with the recording and measuring arrangement having the recording tip, and the inclination of the condyle path on protrusion and medio function is recorded on the measuring/recording plates provided with millimeter paper.

The Bennett value is determined by continuous measurement of the lateral displacement (translation). The length of the condyle path is covered here, and the associated values of the lateral displacement are measured. The measured values found are converted into angle degrees. The intercondylar spacing of the articulator in relation to the measuring/recording plate spacing is taken into account. The angle degrees which have been calculated or taken from the tables can also be used directly for adjusting the articulator.

The recording and measuring arrangement is preferably a displacement-measuring clock whose mechanically operating displacement meter simultaneously functions as a writing stylus, since it has an adjustable lead in a mounting at its tip. Instead of the displacement-measuring clock as the recording and measuring arrangement, it is also possible to use other instruments which are based on electronic, acoustic, or optical features.

Situated at right angles on the cross bar of the lower recording bow are arms which can be displaced in the longitudinal direction and which can be adjusted in their angle of inclination, and which are designed as slide rails in the form of open or partially open profile tubes, preferably square in cross-section, and are arranged on a rocker body such that they can be displaced in the longitudinal direction by means of a spindle, the rocker body being connected via a shaft to the rocker mounting which is secured on the cross bar and which, for the purpose of adjusting the angle of inclination, has, instead of two lockable levelling screws, only one levelling screw provided with a lock nut, and also one or more springs acting counter to the levelling screw. The rocker mounting is described in detail in the above-mentioned U.S. Pat. No. 4,328,620.

The dental recording apparatus according to the invention can be used at the same time as a hinge axis localizer and as a transfer instrument.

Further details and features of the invention are evident from the following description in conjunction with the drawings. The drawings, with reference to which the invention is further explained, depict only preferred embodiments of the apparatus according to the invention. The invention itself is therefore not limited to these preferred embodiments.

DETAILED DESCRIPTION OF THE PREFERRED EMBODIMENTS

Figure 1:
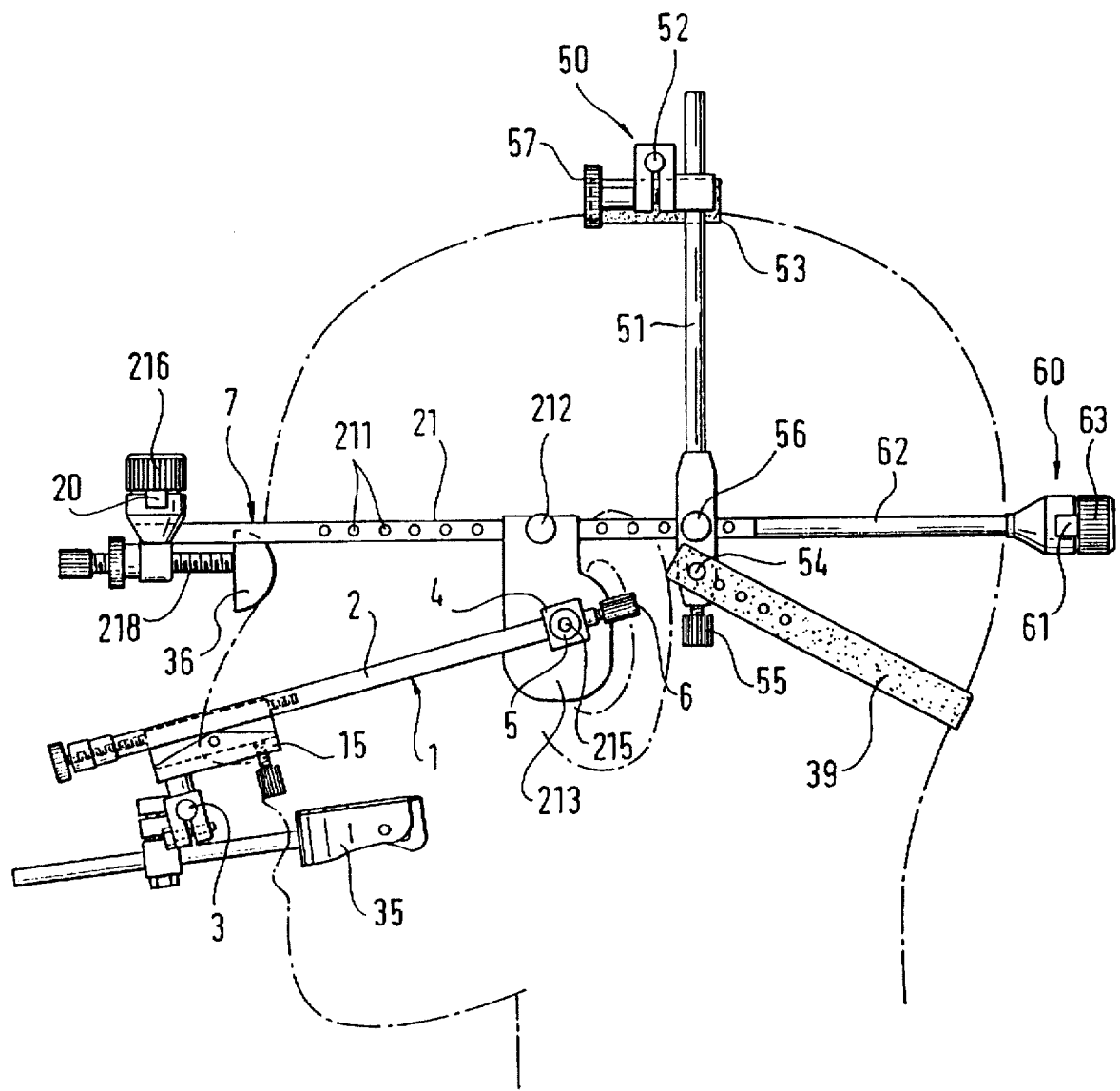
FIG. 1 is a side-view of the dental recording apparatus in reduced scale.
Figure 2:
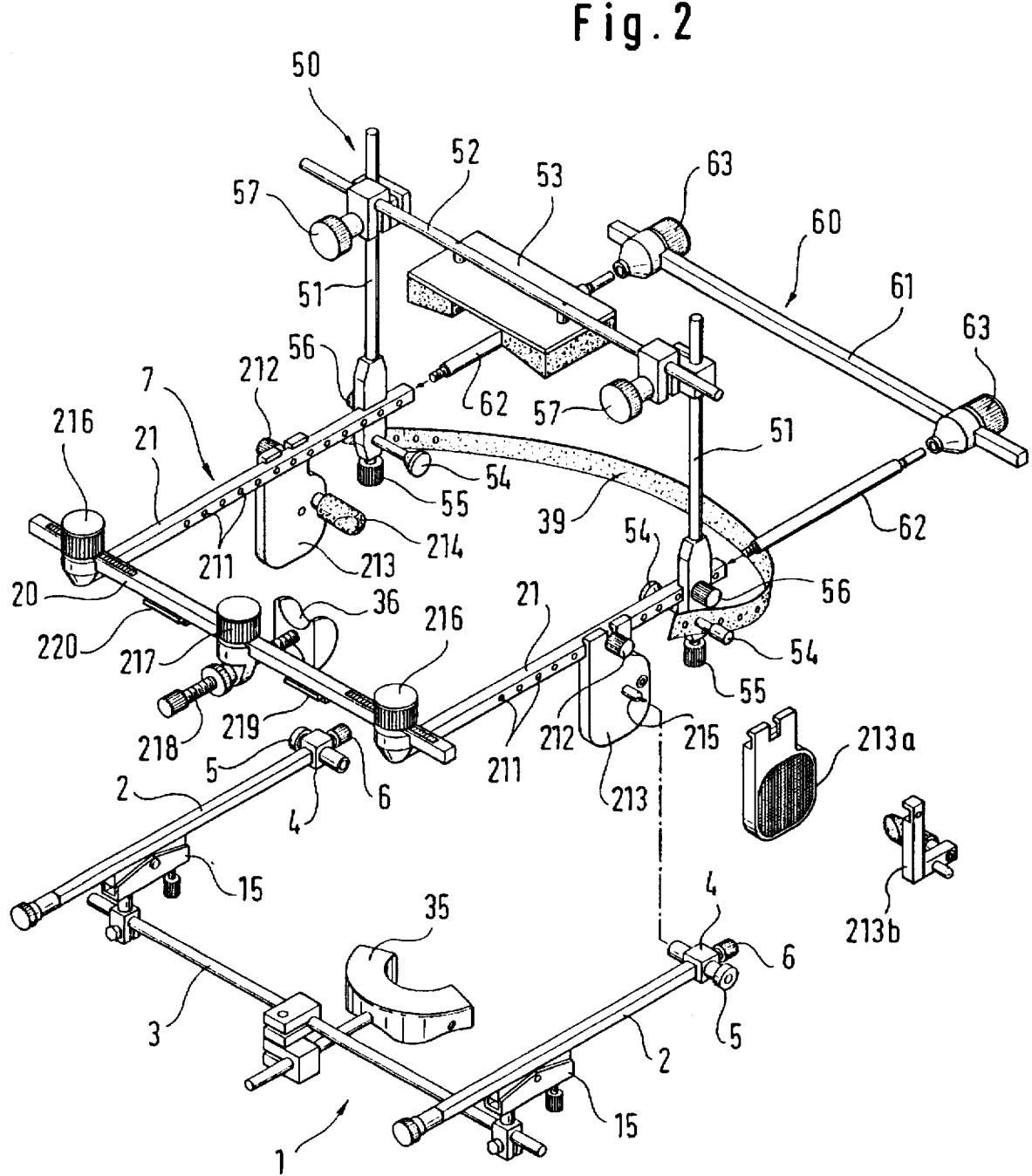
FIG. 2 is a perspective view illustrating upper and lower recording bows of the dental recording apparatus in reduced scale.

FIGS. 1 and 2 show the dental recording apparatus according to a preferred embodiment of the invention consisting of lower recording bow 1 and upper recording bow 7 including vertical frame 50 and rear U-shaped auxiliary frame 60.

The upper recording bow 7 includes side arms 21, front cross bar 20, the positioning means 213 or 213b and the nose bridge support 36 which can be adjusted in the transverse direction and which can be adjusted by means of a spindle 218 fixed on the front cross bar 20 by clamping screw 217. On the front cross bar 20 are further mounted attachment means 219 for tray and attachment means 220 for reference indicator. The front cross bar 20 and the side arms 21 are fixed together by means of clamping screws 216. Preferably the side arms 21 are arranged in such a way that they can only be displaced laterally on the front cross bar 20 of the upper recording bow 7, so that only the spacing between the side arms 21 can be varied in accordance with the shape of the head. The side arms 21 are provided with threaded holes 211 for mounting either the positioning means 213, 213b or the recording plate 213a thereon. Preferably the two side arms 21 of the upper recording bow 7 have a multiplicity of corresponding threaded holes 211 which are arranged at uniform spacings on the two side arms 21 and which are used for securing both the positioning means 213, 213b and also for securing the vertical support bars 51 of the vertical frame 50. The positioning means 213 is constructed in the form of a plate. The positioning means 213b is constructed in the form of an angle profile. The positioning means 213, 213b provided with pin 215 and earplug 214 are affixed to the side arms 21 by means of attachment screws 212 and the corresponding threaded holes 211.

The vertical frame 50 includes the cross bar 52 with head cushion 53 and the vertical support bar 51. At the lower ends of the vertical support bars 51 is the rubber strap 39 which is secured thereon and which is guided round the back of the patient's head to the other side arm. The vertical support bars 51 and the cross bar 52 are fixed together by means of clamping screws 57. Further the vertical support bars 51 and the side arms 21 are fixed together by means of attachment screws 56.

The rear end of the side arms 7 of the upper recording bow 7 are connected with a rear U-shaped auxiliary frame 60 which, for the purpose of parallelization of the side arms 21, can be adjusted to the front spacing between the side arms 21, and which consists of a cross bar 61 and lockable longitudinal bars 62.

The upper recording bow 7, which rests on the bridge of the nose by means of the nose bridge support 36, in this way obtains a firm fit on the head with the side spacers 54 (locked by the locking screws 55) and the head cushion 53.

The lower recording bow 1 can also clearly be seen, this being held by the patient in the mouth via the cast-in tray 35 which is located on the cross bar 3 which is connected with the side arms 2 by means of rocker supports 15. Depending on the width of the head, the side arms 2 of the lower recording bow can be adjusted by displacement on the cross bar 3. The cross bar 3 passes through the rocker mounting 15 which, as has already been stated, is described in detail in U.S. Pat. No. 4,328,620 (Heinz MACK). Situated at the end of the side arm 2 are the attachment means 4 with the sleeves 5 locked by means of locking screws 6 which are later replaced by the measuring/recording arrangements, which are likewise described in detail in the above mentioned U.S. Pat. No. 4,328,620 (Heinz MACK).

In accordance with a further preferred embodiment, the clamping screws 57 with clamping arrangement represented in FIGS. 1 and 2 are replaced by the cross clamps described in detail in the above mentioned U.S. Pat. No. 4,328,620 (Heinz MACK), the screw heads of these cross clamps having the same diameter as the screw heads of the clamping screws 216. Consequently, it is likewise possible to measure off the exact spacing between the clamping screws 216 on the front cross bar 20 of 7, so that the spacings between the cross clamps of the vertical frame 50 correspond, like the spacing between the clamping screws 63 of the rear U-shaped auxiliary frame 60, with the spacings between the clamping screws 216. In this way, it is ensured that both the vertical support bars 51 of 50 and the longitudinal bars 62 of 60 have the same spacings with respect to one another as the side arms 21 of the front part of the upper recording bow.

I claim:

1. A dental recording apparatus for recording movements of the jaw joints in relation to the skull, the apparatus comprising (A) an adjustable upper recording bow securable on the bridge of the nose and on the area of the temples and having a nose bridge support, measuring/recording plates, an upper reference indicator and a rubber strap, and (B) a lower recording bow connected to the movable lower jaw by means of a tray or a clamping arrangement, the lower recording bow having, on both side arms secured on a cross bar, arrangements into which a recording and measuring arrangement is introduced for allowing continuous recording of movements in all 3 planes, for plotting the vertical and horizontal movements and at the same time measuring the axial displacements of the horizontal movements mechanically, electronically, acoustically or optically and recording these via an auxiliary device, (1) the upper recording bow including
   (a) positioning means having an earplug thereon, and pins for positioning of the lower recording bow, the positioning means being replaced later by the measuring/recording plates,
   (b) a perpendicularly arranged vertical frame having support bars connected in an upper area to an adjustable cross bar on which a head cushion is secured, and provided in a lower area with laterally adjustable and lockable side spacers,
   (c) a rear U-shaped auxiliary frame which, for purposes of parallelization of the side arms, is adjustable to a front spacing between the side arms and attachable on the side arms, the U-shaped auxiliary frame comprising a cross bar and lockable longitudinal bar, and
   (d) a nose bridge support adjustable in a longitudinal direction and laterally displacable on the front cross bar, (2) the lower recording bow for positioning on the pins of the positioning means of the upper recording bow including sleeves guided through attachments at a rear end of the side arms, the sleeves being fitted on the pins and locked by means of the locking screws, and (3) the positioning means being replaceable by the measuring/recording plates and, on the lower recording bow, the sleeves being replaceable by the recording and measuring arrangements after casting-on of the tray or securing of a corresponding clamping arrangement on the lower jaw, and after positioning of the upper recording bow and of the lower recording bow.

2. The dental recording apparatus according to claim 1, wherein the side arms of the upper recording bow are arranged such that they can only be displaced laterally on the front cross bar of the upper recording bow, only the spacing between the side arms being variable in accordance with the shape of the head.

3. The dental recording apparatus according to claim 1, wherein the two side arms of the upper recording bow include a multiplicity of corresponding threaded holes arranged at uniform spacings on the two side arms, for securing both the positioning means and for securing the vertical support bars of the vertical frame.

* * * * *